United States Patent [19]

Hermentin et al.

[11] Patent Number: 5,672,687

[45] Date of Patent: Sep. 30, 1997

[54] MAGNETIC PROTEIN CONJUGATES, A PROCESS FOR THE PREPARATION THEREOF, AND THE USE THEREOF

[75] Inventors: Peter Hermentin, Marburg; Reiner Dönges, Dautphetal; Karlheinz Enssle, Marburg; Roland Kurrle, Marburg; Friedrich Robert Seiler, Marburg, all of Germany

[73] Assignee: Behringwerke Aktiengesellschaft, Marburg, Germany

[21] Appl. No.: 375,232

[22] Filed: Jan. 19, 1995

Related U.S. Application Data

[63] Continuation of Ser. No. 182,368, Jan. 18, 1994, abandoned, which is a continuation of Ser. No. 832,625, Feb. 12, 1992, abandoned, which is a continuation of Ser. No. 320,450, Mar. 8, 1989, abandoned.

[30] Foreign Application Priority Data

Mar. 10, 1988 [DE] Germany ............... 38 07 904

[51] Int. Cl.$^6$ .......... C07K 17/06; G01N 33/547; G01N 33/553; A61K 39/44
[52] U.S. Cl. ................ 530/391.5; 530/391.1; 530/391.3; 530/404; 530/405; 530/408; 530/409; 435/181; 436/526; 424/9.34
[58] Field of Search .............. 530/391.1, 391.3, 530/391.5, 404, 405, 408, 409; 435/174, 181; 436/526; 424/9.34

[56] References Cited

U.S. PATENT DOCUMENTS

| 4,659,839 | 4/1987 | Nicolotti et al. | 548/546 |
|---|---|---|---|
| 4,671,958 | 6/1987 | Rodewell et al. | 424/85.91 |
| 4,698,302 | 10/1987 | Whitehead et al. | 435/94 |
| 4,735,796 | 4/1988 | Gordon | 424/9 |
| 5,002,883 | 3/1991 | Bieniarz et al. | 435/176 |

FOREIGN PATENT DOCUMENTS

| 0089880 | 9/1983 | European Pat. Off. | A61K 39/44 |
|---|---|---|---|
| 109653 | 5/1984 | European Pat. Off. | C12N 11/06 |
| 0125995 | 11/1984 | European Pat. Off. | G01N 33/54 |
| 83/03920 | 11/1983 | WIPO | H01F 1/09 |
| WO 87/02063 | 4/1987 | WIPO | C12Q 1/00 |

OTHER PUBLICATIONS

Vartdal et al. Transplantation, vol. 43, No. 3 (1978).
Boyum, Scand. J. Immunol., vol. 5, Suppl. 5 (1976).
Kvalheim et al., Cancer Research, vol. 47 (1987) pp. 846–851.
Treleaven et al., "Removal of neuroblastoma cells from bone marrow with monoclonal antibodies conjugated to magnetic microspheres," The Lancet, 70, 73 (1984).
Blair et al (1983) J. Immunol. Methods 59:129–143.
Imagawa et al (1982) J. Appl. Biochem. 4:41–57.
Keller et al (1975) Hel. Chim. Acta 58 (Fasc. 2) No. 62–63:531–541.

*Primary Examiner*—Kay K. A. Kim
*Attorney, Agent, or Firm*—Finnegan, Henderson, Farabow, Garrett & Dunner, L.L.P.

[57] ABSTRACT

The invention relates to magnetic protein conjugates of the formula I

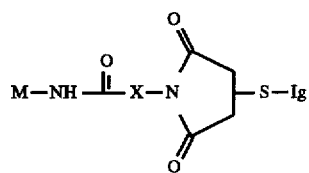

in which M represents a dispersible magnetically reacting material or particle which carries aminogroups, Ig represents a protein which carries one or more mercapto groups, and X represents an organic chemical structure which links the two ligands by chemical means, to a process for the preparation of protein conjugates of the formula I, and to the use of conjugates of this type for removing cells or soluble bioorganic molecules or components from aqueous salt solutions or body fluids, and to the use thereof within the framework of a diagnostic method or as a diagnostic aid.

13 Claims, 3 Drawing Sheets

MAGNETIC PROTEIN CONJUGATES, A PROCESS FOR THE PREPARATION THEREOF, AND THE USE THEREOF

This application is a continuation, of application Ser. No. 08/182,368, filed Jan. 18, 1994, now abandoned, which is a continuation of application Ser. No. 07/832,625, filed Feb. 12, 1992, now abandoned, which is a continuation of application Ser. No. 07/320,450, filed Mar. 8, 1989, now abandoned.

The invention relates to magnetic protein conjugates of the general formula I

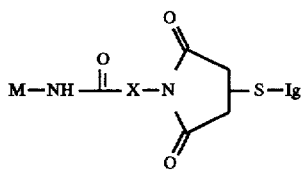

to which the following applies:

M is a dispersible magnetically reacting material or particle which carries amino groups, Ig is a protein which carries one or more mercapto groups, and X is an organic chemical structure which links the two ligands by chemical means.

X is preferably an aliphatic, aromatic, alicyclic, alicyclic-aliphatic or aromatic-aliphatic spacer which can optionally be substituted in a suitable manner in each case, preferably —$(CH_2)_n$— with n=1–8, preferably with n=1–5 and particularly preferably with n=2 or 3, or X is preferably phenylene or substituted phenylene, it being possible for the two ligands to be in the ortho, meta or para positions, and it being possible for a substituent which is optionally present in the phenylene ring to be a methyl, hydroxyl, methoxy, acetoxy, nitro or cyano group or a chlorine or bromine atom, or X is preferably phenylene—$(CH_2)_n$— with n=1–5, preferably with n=3, with the phenylene group being linked to the succinimidyl group, or X is preferably —CHR—, where R represents an amino acid side chain, preferably the side chain of the amino acids alanine, serine, threonine or methionine and particularly preferably the side chain of alanine, or X is preferably methylenecyclohexyl, where the methylene group is linked to the succinimidyl group and, with respect to the carbonyl group linked to the cyclohexyl ring, is preferably linked in position 4 of the cyclohexyl ring.

The nature of X can also be such that it can be cleaved by chemical or enzymatic means.

Ig can be a protein in which the mercapto groups either are present in the natural way or are generated by reduction of disulfide linkages or are introduced by a chemical reaction.

Ig is, in particular, an immunoglobulin or immunoglobulin residue, preferably a monoclonal antibody or a Fab, Fab' or F(ab')$_2$ fragment, an antigen or a residue of an enzyme, hormone, lectin or growth factor.

Ig is preferably a monoclonal antibody of the IgG or IgM class, in particular a monoclonal antibody which is directed against an antigen which is present in dissolved form in aqueous salt solutions or body fluids, or a monoclonal antibody which is directed against an antigen which is expressed on cells, it being possible for the cells expressing the antigen to be, in particular, cells of the myeloid or lymphatic system, cells of the peripheral blood, in particular B lymphocytes, T lymphocytes or the precursor cells thereof, or tumor cells, in particular tumor cells of the bone marrow. Such cells can also be erythrocytes, bacteria, mycoplasmas or protozoa. However, viruses are also to be understood to be cells within the scope of the invention.

M is preferably a dispersible particle with a metal oxide core and with an enveloping coat carrying amino groups, it being possible for the metal oxide core to include a group of paramagnetic substances, preferably a particle whose diameter is between about 0.1μ and about 100μ, but preferably between about 0.1μ and about 1.5 μ.

The invention also relates to a process for the preparation of a magnetic protein conjugate of the general formula I and to the use of a conjugate of the formula I for the specific removal of cells or soluble antigens, receptors, substrates, cofactors or carbohydrate determinants from aqueous salt solutions or body fluids, and to the use within the framework of a diagnostic method or as a diagnostic aid, and, in particular, to the use for bone marrow depletion or for HLA typing.

Bone marrow transplantation is often the only therapeutic option for, inter alia, the treatment of certain types of leukemia and of panmyelopathy (panmyelophthisis).

In cases of leukemia and certain lymphoid neoplasias, the patients have hitherto been subjected to whole-body irradiation with an extremely high dose and/or to aggressive chemotherapy. With a treatment of this type the normal stem cells of the bone marrow, the precursors of all blood cells, are completely destroyed. Hence bone marrow from a suitable donor is reinfused into the patient, and cells from this colonize the medullary cavities of the recipient and thus permit redevelopment of the hemopoietic and immune systems. This method is called allogeneic bone marrow transplantation.

The high risk of allogeneic bone marrow transplantation derives, inter alia, from the T lymphocytes of the donor, which are carried over into the patient in the reinfused bone marrow and which recognize the cells of the recipient as foreign and thus attack and destroy them. This bone marrow intolerance, which is often life-threatening for the patient, is called the graft-versus-host reaction or graft-versus-host disease (GVHD). The risks of this graft-versus-host disease can, on the one hand, be diminished by, if possible, reinfusing accurately typed bone marrow from particularly suitable donors, usually from among the relatives, into the patient. However, on the other hand, they can also be reduced by selectively eliminating undesired cell populations, as may be represented by, for example, T lymphocytes of the donor bone marrow, before reinfusion into the patient. This elimination of donor T cells can be carried out, for example, by selective lysis, in the presence of complement, of the cells which are to be removed, or by selective killing of the T cells with the aid of so-called immunotoxins, or by another method, for example by magnetic cell depletion of the bone marrow.

Bone marrow cell depletion of this type can be carried out in a relatively straightforward manner, in such a way that the bone marrow is incubated with a monoclonal mouse antibody which, for example, is directed specifically against the T cells of the bone marrow and, as a consequence, binds only to the T cells. T cells of this type, to which monoclonal mouse antibodies are attached, can now be removed in a second step by incubating them for example with rabbit anti-mouse immunoglobulin which is bound to magnetic particles, by which means the magnetic material is attached in a specific manner to the T lymphocytes so that they can be removed from the bone marrow with the aid of a magnet (in this context, see Vartdal et al., Transplantation (1987), 43, 366–371 and the literature cited therein).

It is also possible in an analogous manner to remove from the bone marrow other cell populations, for example tumor cells, which is of importance for what is called autologous bone marrow transplantation (in this context, see Kvalheim et al., Cancer Research (1987), 47, 846–851 and the literature cited therein). Moreover, it is also possible, as described by Kvalheim et al., ibid., to bind the monoclonal antibody which recognizes the tumor cells directly onto the magnetic particles so that the abovementioned second antibody (rabbit anti-mouse) is no longer necessary.

The method, described above, for bone marrow depletion with the aid of monoclonal or polyclonal antibodies which are bound to magnetic particles is still very new and requires further development and testing. A very wide variety of types of magnetic particles suitable for this purpose are now commercially available, and the preparation thereof has been described more than once in the patent literature (see, for example, Chagnon et al., EP 0,125,995 A2 (priority U.S. Pat. No. 493,991 of May 12, 1983), Advanced Magnetics, or Ughelstad et al., WO 8,303,920 of Nov. 10, 1983, SINTEF). It is known of these magnetic particles that they are composed of a metal oxide core, in which paramagnetic substances may be included, and that the core is surrounded by an enveloping coat which may carry reactive groups such as, for example, aminophenyl, amino, carboxyl, hydroxyl or sulfhydryl groups, which can be used for coupling proteins (Chagnon et al., EP 0,125,995 A2).

It is known, for example, that particles carrying carboxyl groups can be induced to react with amino groups of proteins in the presence of a condensing agent (Chagnon et al., EP 0,125,995 A2).

Also known is the coupling of proteins to the magnetic particles carrying amino groups, by use of glutaraldehyde, the coupling taking place via the amino groups in each case (Chagnon et al., EP 0,125,995 A2).

Furthermore, it is known that particles carrying hydroxyl groups can be activated by reaction with p-toluenesulfonyl chloride, and that particles activated in this way can be induced to react with amino groups of proteins (Kvalheim et al., Cancer Research (1987), 47, 846–851).

It is common to all these coupling methods that the protein is, in each case, linked to the particles via its free amino groups. However, coupling of this type via amino groups may be a considerable disadvantage with monoclonal antibodies because, in this case, occasionally the specificity and reactivity of the antibodies is impaired. This is a consequence of the fact that the amino groups in an antibody are distributed more or less at random over the entire molecule, and thus are also located in the antigen-binding site of the Fab fragment, which brings about a loss of specificity where there is coupling via these amino groups.

It is furthermore known that antibodies can be taken up on magnetic particles even without chemical linkage, purely by adsorption, if the particles are enveloped in a styrene/divinylbenzene copolymer, because protein is known to bind non-specifically to polystyrene.

However, even with this method an impairment of the antibody specificity and reactivity must be expected. Another serious disadvantage of this method comprises, however, the possibility that antibodies bound by adsorption become detached again during bone marrow depletion and thus are also administered to the patient on reinfusion of the depleted bone marrow, which might result in serious side reactions, especially where there has been a previous attempt at therapy with monoclonal antibodies. However, this problem is known, and the aim is to overcome it by covalent linkage of the antibodies to the magnetic particles.

It is also known that magnetic particles with a polystyrene envelope have the serious disadvantage that they tend to aggregate and, moreover, attach themselves non-specifically to cells.

Based on this prior art, the object of the present invention is to develop a method in which monoclonal antibodies are coupled to magnetic particles a) covalently and b) not via their amino groups. Hence, in other words, the object of the present invention is to find a coupling method in which the antigen binding site of the antibody is not altered, or the coupling of the antibody takes place away from the antigen binding site.

This object according to the invention is achieved by the preparation of magnetic protein conjugates of the general formula I on page 1.

It has now been found that magnetic particles which carry as reactive groups free amino groups can be converted in a straightforward manner into magnetic particles which carry as reactive groups maleimido groups. Particles of this kind are new.

It has additionally been found that magnetic particles which carry maleimido groups can be conjugated without difficulty with proteins which have mercapto groups, it being possible for the mercapto groups in the protein to be either already present naturally or introduced by chemical means or generated by reduction of disulfide linkages which are present.

In particular, it has been found that magnetic particles which carry maleimido groups can be conjugated without difficulty with monoclonal antibodies if the interchain disulfide linkages of the antibodies are converted by selective reduction into free SH groups which can be induced to react with the maleimido groups of the magnetic particles to form a stable thioether linkage. This way of coupling monoclonal antibodies to magnetic particles is likewise new.

It has been found, surprisingly, that the specificity and reactivity of the antibodies coupled to magnetic particles via thioether linkages is completely retained because the coupling of the antibody via its hinge region does not alter or impair its antigen-binding site. Herein lies a particular advantage of the invention compared with the coupling methods hitherto disclosed, in which the antibodies are, as described above, taken up on magnetic particles either purely by adsorption or by reaction of their amino groups, which may impair both the specificity and the reactivity of the conjugated antibodies. Moreover, compared with coupling by adsorption, the present invention has the advantage that the antibodies are chemically bonded to the magnetic particles and, as a consequence, do not become detached from the particles when magnetic antibody conjugates according to the invention are used, for example for bone marrow depletion.

It has additionally been found that the magnetic antibody conjugates according to the invention prove to be particularly advantageous, for example for the depletion of bone marrow, because of their high specificity.

In addition, it has been found that the magnetic antibody conjugates according to the invention also prove advantageous, because of their high specificity, within the framework of a diagnostic method or as a diagnostic aid, especially, for example, for HLA typing.

The preparation of magnetic antibody conjugates according to the invention is described hereinafter by way of example for various monoclonal antibodies which are directed against cells of the bone marrow; the specified examples do not, however, restrict the invention. In addition, the use of the magnetic antibody conjugates, which have been prepared by way of example, for the depletion of cells of the bone marrow and for HLA typing is likewise described by way of example without restricting the use to the specified examples.

Process for the preparation of a magnetic protein conjugate of the general formula I Magnetic particles M carrying amino groups are reacted in a suitable solvent with a maleimido spacer of the general formula II

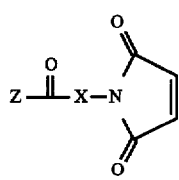

which reacts with amino groups and in which Z is a suitable reactive leaving group, with the formation of an amide linkage, to give a compound of the general formula III

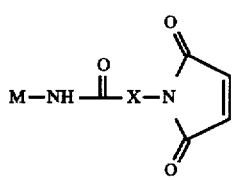

which is finally reacted, in a suitable aqueous salt-containing solvent which does not denature proteins, such as, for example, physiological saline or a phosphate-buffered saline, with a protein Ig carrying mercapto groups to give a compound of the general formula I.

The nature of solvents suitable for the coupling of a compound of the formula II to magnetic particles must be such that the solvent which is used does not impair the physical and magnetic properties of the magnetic particles which are used for the coupling in each case, especially their size, dispersibility and surface characteristics. An example of a solvent found suitable for magnetic particles as described, for example, in EP 0,125,995 A2 or WO 8,303,920 is a mixture of water and dimethylformamide, where the substituent Z in the formula II is, for example and preferably, succinimidyloxy. However, another possible example of a suitable solvent is anhydrous acetone, in which case the substituent Z in the formula II can, besides succinimidyloxy, also be a halogen such as, for example, chlorine or bromine, or a pseudohalide such as, for example, cyanide, or an acyl group such as, for example, acetyl or p-nitrobenzoyl, or another reactive leaving group such as, for example, a tosyl group, with the reaction being carried out in all the cases where Z is not succinimidyloxy preferably in the presence of a suitable base such as, for example, sodium carbonate.

Method for cell depletion

A suspension of a cell mixture which is to be depleted, in a salt-containing, preferably physiological aqueous solution or in a body fluid, is incubated with a compound of the formula I at a suitable temperature between, for example, 0° C. and 40° C., preferably with shaking, likewise preferably under sterile conditions, for a suitable period, and then the magnetic particles are removed from the solution by a suitable magnet.

Examples of suitable temperatures are 0° C., room temperature or 37° C., but room temperature is preferred. The duration of the incubation depends in each case on the incubation temperature used and on the binding reactivity of the antibody and may be, for example, from a few minutes up to, for example, 2 hours. Incubation is preferably carried out at, for example, room temperature for a period of, for example, 10 to 20 minutes.

Method for isolating soluble bioorganic molecules

This method essentially follows the method for cell depletion.

EXAMPLES

The examples which follow serve to illustrate the invention further but do not restrict the invention.

Magnetic particles which have been induced to react in the manner described with monoclonal antibodies are called "magnetobeads" hereinafter, with their specificity being indicated in each case by prefixing the particular antibody name.

EXAMPLE 1

Conjugation of magnetic particles according to EP 0,125, 995 A2 using a gamma-maleimidobutyrate spacer 0.5 ml of a commercially available suspension of magnetic particles (BioMag M4100, Sebak®) was washed 3× with phosphate-buffered saline pH 7.2 (PBS) and resuspended in 6 ml of PBS. To this suspension was added a freshly prepared solution of 20 mg N-(gamma-maleimidobutyryloxy)succinimide (GMBS, Calbiochem) in 4 ml of dry dimethylformamide, and the mixture was shaken at room temperature for 1 h. The particles were then spun down at 3000×g, washed 3× with 20 ml of PBS each time and resuspended in 6 ml of PBS.

EXAMPLE 2

General procedure for coupling monoclonal antibodies* to magnetic particles carrying maleimido groups from Example 1

*) Note: All the monoclonal antibodies used were lyophilized in a concentration of 1 mg/ml in a solution of 0.1 mol/l sodium citrate buffer pH 6.6 and 50 g/l sucrose.

1 mg of lyophilized monoclonal antibody was dissolved in 0.5 ml of water, 2 mg of dithiothreitol were added, and the mixture was incubated at room temperature for 30 min. The reduced antibody was isolated by means of gel filtration on Sephadex G25 in isotonic saline pH 7.2 in an elution volume of 4 ml, and was added to the suspension of magnetic particles prepared as in Example 1. The mixture (10 ml) was incubated at room temperature for 45 min, with shaking. The particles were then spun down at 3500×g, washed 3× with 20 ml of PBS each time, resuspended in 10 ml of PBS pH 7.2, and stored at 4° C.

Where appropriate, 0.2% sodium azide or 0.2% sodium azide +0.1% BSA (bovine serum albumin)+0.2% Tween 20 was added to the suspension.

The monoclonal antibodies coupled as in Example 2 are summarized in Table 1.

TABLE 1

| Magnetobeads prepared as in Example 2 | | |
|---|---|---|
| Monoclonal antibody | Class and isotype | Specificity |
| BMA 0110 | IgG2b | CD2 |
| BMA 0111 | IgG1 | CD2 |
| BMA 030 | IgG2a | CD3 |
| BMA 033 | IgG3 | CD3 |
| BMA 031 | IgG2b | TCR |
| BMA 041 | IgM | CD4 |
| BMA 0117 | IgG2a | CD7 |

TABLE 1-continued

Magnetobeads prepared as in Example 2

| Monoclonal antibody | Class and isotype | Specificity |
|---|---|---|
| BMA 081 | IgG2a | CD8 |
| VIL-A1 | IgM | CD10 |
| SV393 | IgG1 | Beta-2-M |
| BMA 022 | IgG2a | HLA-DR |
| BMA 0210 | IgM | monocytes |
| 84-24/91-8 | IgG1 | TSH |
| BB 10 | IgG2b | CD10/CALLA |
| BMA 0160 | IgM | Glycophorin A |
| BMA 0112 | IgG1 | CD7 |
| 704/152/5 | IgG3 | Neuroblastoma |
| 575/931/2 | IgG1 | SCLC |
| A-h-TSH 5404 | IgG1 | TSH |
| 383/44 | IgG1 | IgE |
| 393/57 | IgG2b | IgE |
| 84-9/6 | IgG2a | IgE |
| 209/2 | IgG2a | CD2 |
| RAM | polyclonal | mouse gamma-globulin | explanation of abbreviations see Table 2

EXAMPLE 3

Positive reaction of BMA 041 magnetobeads with T cells

40 µl of a suspension of BMA 041 magnetobeads in PBS prepared as in Example 2 were incubated with 120 µl of a T cell suspension (clone 5/87-7-A3; $CD4^+$, $CD8^-$, $CD2^+$, $CD3^+$, T-cell receptor-positive; $1 \times 10^4$ cells/µl in RPMI 1640) at room temperature for 10 min, with shaking, and, without delay, were inspected under the microscope in a counting chamber and photographed. The cells had formed rosettes or aggregates with the magnetic particles.

EXAMPLE 4

Negative reaction of BMA 041 magnetobeads with B cells

40 µl of a suspension of BMA 041 magnetobeads in PBS prepared as in Example 2 were incubated with 120 µl of a B cell suspension (B cell line GR, $1 \times 10^4$ cells/µl in RPMI 1640) as in Example 3 and were then inspected under the microscope and photographed. No formation of rosettes or aggregates was observed.

EXAMPLE 5

Positive reaction of BMA 081 magnetobeads with T cells

40 µl of a suspension of BMA 081 magnetobeads prepared as in Example 2 were incubated as in Example 3 with T cells (clone 5/87-4-B6; $CD8^+$, $CD4^-$, $CD2^+$, $CD3^+$, T-cell receptor-positive) and then inspected under the microscope and photographed. The negative control was B cells analogous to Example 4 (B cell line GR). The T-cell receptor-positive cells had formed rosettes or aggregates with the magnetic particles. No formation of rosettes or aggregates was observed with the negative control.

EXAMPLE 6

Positive reaction of BMA 031 magnetobeads with T cells

40 µl of a suspension of BMA 031 magnetobeads prepared as in Example 2 were incubated in analogy to Example 3 with T cells (clone 5/87-4-B6; $CD8^+$, $CD4^-$, $CD2^+$, $CD3^+$, T-cell receptor-positive) and then inspected under the microscope and photographed. The negative control was B cells analogous to Example 4 (B cell line GR). The antigen-positive cells had again formed rosettes or aggregates with the magnetic particles; the antigen-negative cells were unassociated.

EXAMPLE 7

Depletion of cell populations from mononuclear cells

Mononuclear cells (MNC) were isolated from freshly donated human blood on a Ficoll gradient in a manner known per se (Boyum, Scand. J. Immunol. (1976), Suppl. 5, 9–15).

For the depletion, $3 \times 10^7$ MNC in 2 ml of PBS containing 1% BSA (w/v, Seromed) in plastic tubes (Falcon, No. 2051) were mixed with 1 ml of a suspension of 2 mg/mL magnetobeads in PBS and incubated at room temperature, shaking continuously, for 15 min. The magnetobeads and the cells bound thereto were then removed with the aid of a permanent magnet. The cells remaining in suspension were pelleted at 400×g and resuspended in a suitable medium, for example PBS or RPMI 1640. The depletion efficiency was determined by means of indirect immunofluorescence in a cytofluorograph (Ortho).

For this purpose, before and after depletion of a particular cell population $1 \times 10^6$ cells were labeled with 1–10 µg/ml first antibody (a monoclonal antibody of suitable specificity in each case) and then with 10–50 µg/ml second antibody (rabbit anti-mouse immunoglobulin, $F(ab)_2$ fragment, FITC-labelled, Behringwerke) in a manner known per se and evaluated in a cytofluorograph, and the depletion efficiencies were determined to be above 95% in each case.

The cells depleted as in Example 7 are listed in Table 2.

The results achieved for the depletion with BMA 041 (anti-CD4, Behringwerke AG) magnetobeads and BMA 081 (anti-CD8, Behringwerke AG) magnetobeads are depicted by way of example in FIG. 1. This entailed the depletion efficiency being determined by labeling the unbound cell population in each case with BMA 031 (anti-T-cell receptor, Behringwerke AG), BMA 041 or BMA 081. After incubation with FITC-labeled second antibody (see above) the fluorescence intensity in each case was evaluated in a cytofluorograph with linear amplification.

TABLE 2

Depletion of cells by means of magnetobeads prepared as in Example 2

| Coupled monoclonal antibody | Antigen recognized (specificity) | Depleted cell population |
|---|---|---|
| BMA 0110 | CD2 | $CD2^+$-T-cells |
| BMA 0111 | CD2 | $CD2^+$-T-cells |
| BMA 030 | CD3 | $CD3^+$-T-cells |
| BMA 033 | CD3 | $CD3^+$-T-cells |
| BMA 031 | TCR | $TCR^+$-T-cells |
| BMA 041 | CD4 | $CD4^+$-T-cells |
| BMA 0117 | CD7 | $CD7^+$-T-cells |
| BMA 081 | CD8 | $CD8^+$-T-cells |
| VIL-A1 | CD10 | $CD10^+$-B-cells |
| SV 393 | Beta-2-M | HLA-class $I^+$-cells |
| BMA 022 | HLA-DR | HLA-class $II^+$-cells |
| BMA 0210 | monocytes | monocytes |
| BB 10 | CD10/CALLA | $CD10^+$- or $CALLA^+$-cells |
| BMA 0160 | Glycophorin A | erythrocytes |
| BMA 0112 | CD7 | $CD7^+$-cells |
| 704/152/5 | Neuroblastoma | Neuroblastoma-cells |
| 209/2 | CD2 | $CD2^+$- cells | explanation of abbreviations:
CD: clusters of differentiation
TCR: T-cell receptor
Beta-2-M: $\beta_2$-microglobulin
HLA-DR: human leucocyte antigen, subclass DR
TSH: thyroid-stimulating hormone
CALLA: common acute lymphoblastic leukaemia antigen
SCLC: small cell lung cancer
IgE: immunoglobulin E
RAM: rabbit anti-mouse

EXAMPLE 8

Detection of the proliferation of T cells in culture after incubation with uncoupled magnetic particles (BioMag M4100, Sebak®) in Mononuclear cells were isolated from human blood in analogy to Example 7 and incubated with a suspension of uncoupled magnetic particles (BioMag M4100, Sebak$^R$) in analogy to Example 7. The magnetic particles were then removed with the aid of a permanent magnet. The remaining MNC were incubated in 96-well flat-base titer plates (Nunc) at a concentration in each case of $1 \times 10^5$ MNC per well in serum-free culture medium (Iscove, Behring modification) in the presence of pokeweed mitogen (PWM, Gibco; 1:3000 final dilution) or of 10 µg/ml phytohemagglutinin (PHA, Wellcome) in a $CO_2$ incubator at 37° C. for 64 hours. After a culture time of 48 hours $2.7 \times 10^3$ Bq of $^{14}$C-thymidine (Amersham) were added to each of the cultures. After a further culture time of 14 hours, the cells were filtered off with suction on glass fiber filter disks using a cell harvester (Innotec). The radioactivity on the filters was determined in a β counter (Packard) after addition of scintillation fluid.

FIG. 2 shows the evaluation of an experiment of this type and demonstrates that the stimulation of MNC with PHA or PWM is not impaired by depletion with uncoupled magnetic particles (BioMag M4100, Sebak®).

EXAMPLE 9

Detection of the proliferation of T cells in culture in the presence of uncoupled magnetic particles (BioMag M4100, Sebak®).

Various amounts of uncoupled magnetic particles (BioMag M4100, Sebak®) were added to MNC which were then distributed in 96-well plates and cultivated with PHA (10 µg/ml), BMA 030 (Behringwerke, mitogen for T lymphocytes) (0.01 µg/ml) or Staphylococcus aureus capsid (SAC, Behringwerke, mitogen for B lymphocytes, final dilution 1:3000) in analogy to Example 8.

It is evident from FIG. 3 that magnetic particles (BioMag M4100, Sebak®) do not, at a concentration of 2–20 µg/ml, have an adverse effect on the proliferation of B and T cells.

Figure 1:
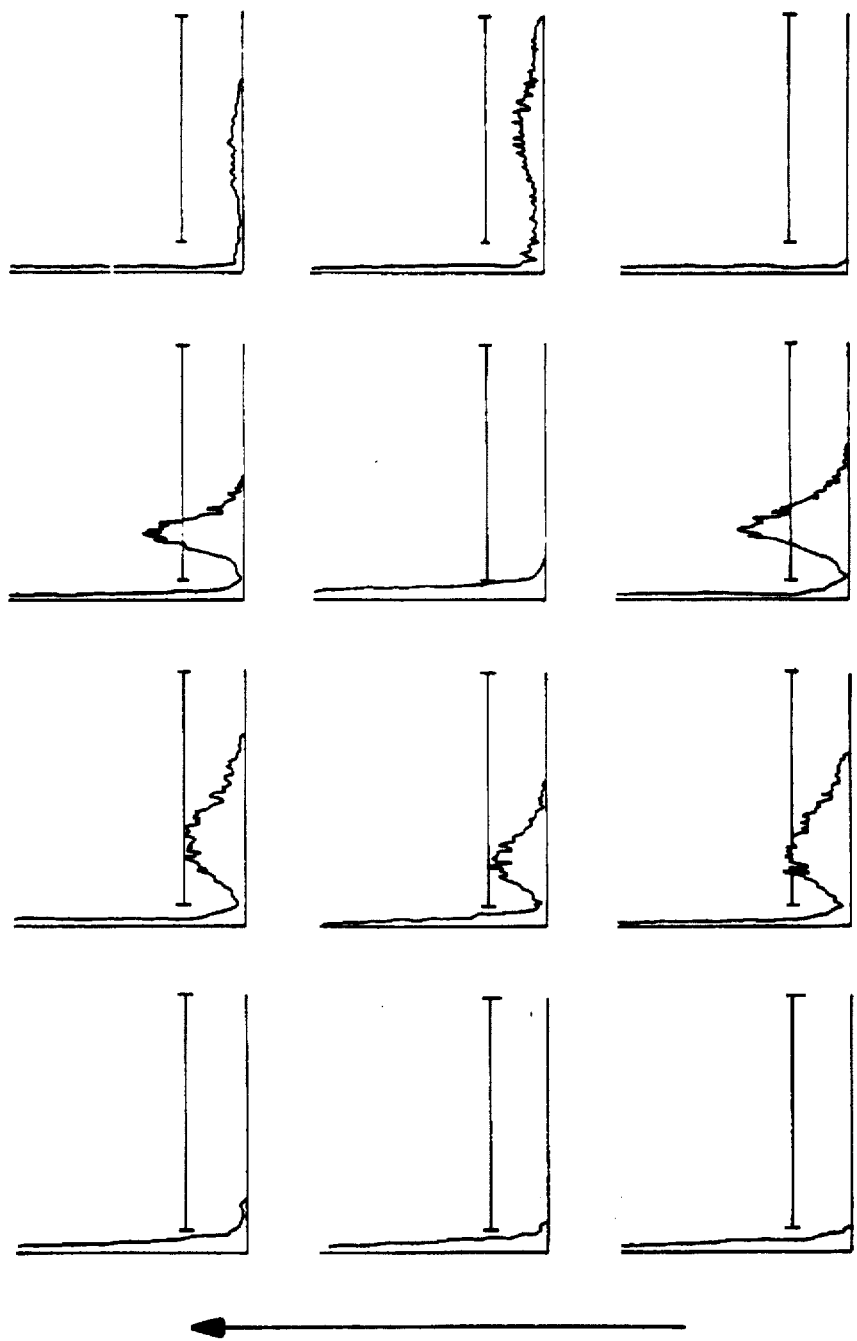
FIG. 1: Depletion of T cell subpopulations with BMA 041 and BMA 081 magnetobeads PBL: original cell population CD4⁻: population after depletion with BMA 041 magnetobeads CD8⁻: population after depletion with BMA 081 magnetobeads
Figure 2:
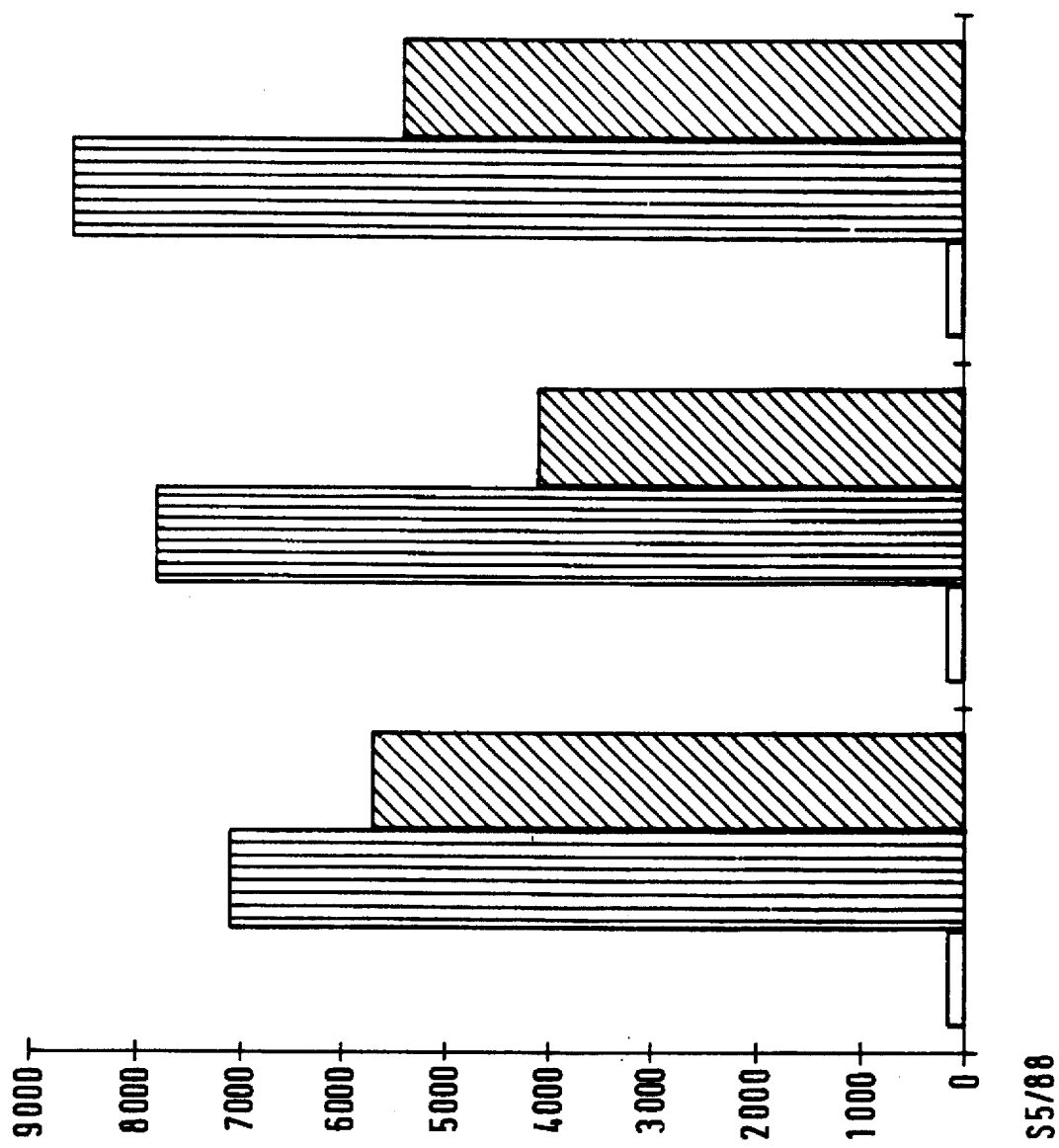
FIG. 2: Proliferation of T cells in culture after incubation with uncoupled magnetic particles (BioMag M4100, Sebak®) and stimulation with phytohemagglutinin (PHA) or pokeweed mitogen (PWM) compared with medium control
Figure 3:
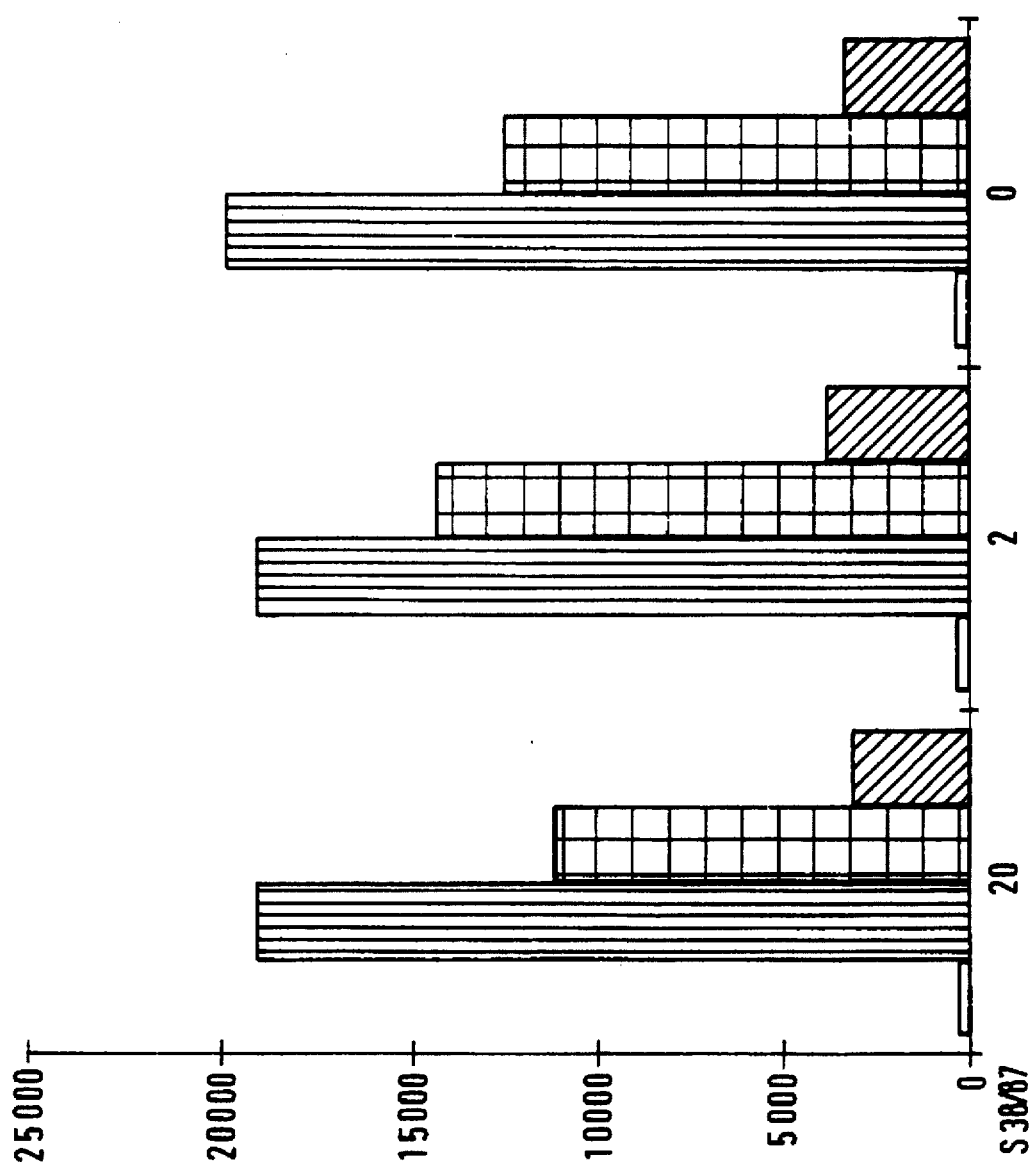
FIG. 3: Proliferation of T cells in culture in the presence of uncoupled magnetic particles (BioMag M4100, Sebak®) after stimulation with phytohemagglutinin (PHA), anti-CD3 monoclonal antibody BMA 030, or Staphylococcus aureus capsid (SAC) compared with medium control

We claim:

1. A magnetic protein conjugate of the formula I:

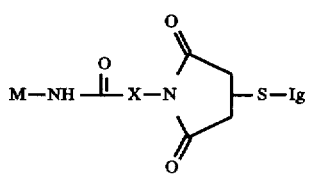

in which

M is a dispersible magnetically reacting material or a magnetic particle which carries amino groups, Ig is an immunoglobulin having one or more mercapto groups present in its hinge region, said one or more mercapto groups produced by the reduction of interchain disulfide linkages, and X is selected from the group consisting of —(CH$_2$)$_3$—, phenylene, cyclohexane—CH$_2$—, and —CH$_2$—CH$_2$—CH$_2$—phenylene—, wherein X chemically links the magnetic particle M covalently with said Ig.

2. The magnetic protein conjugate as claimed in claim 1, wherein Ig is a monoclonal antibody of the IgG or IgM class.

3. The magnetic protein conjugate as claimed in claim 1, wherein Ig is a monoclonal antibody directed against a soluble antigen present in aqueous salt solutions or body fluids.

4. The magnetic protein conjugate as claimed in claim 1, wherein Ig is a monoclonal antibody directed against an antigen which is expressed on cells.

5. The magnetic protein conjugate as claimed in claim 4, wherein Ig is a monoclonal antibody directed against an antigen which is expressed on bacteria, mycoplasmas, protozoa, or viruses.

6. The magnetic protein conjugate as claimed in claim 4, wherein said antigen is expressed on cells of the myeloid system, cells of the lymphatic system, or cells of the peripheral blood.

7. The magnetic protein conjugate as claimed in claim 4, wherein said antigen is expressed on B lymphocytes, T lymphocytes, precursor cells of B or T lymphocytes, or on tumor cells.

8. The magnetic protein conjugate as claimed in claim 4, wherein said antigen is expressed on tumor cells of the bone marrow.

9. The magnetic protein conjugate as claimed in claim 1, wherein M is a dispersible particle with a metal oxide core and an enveloping coat carrying amino groups.

10. The magnetic protein conjugate as claimed in claim 9, wherein said metal oxide core comprises a group of paramagnetic substances.

11. The magnetic protein conjugate as claimed in claim 9, wherein the diameter of the particles is between about 0.1µ and about 100 µ.

12. The magnetic protein conjugate as claimed in claim 11, wherein the diameter of the particles is between about 0.1µ and about 1.5µ.

13. A process for the preparation of a magnetic protein conjugate of the formula I

11

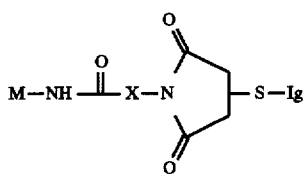

I

12

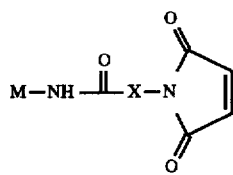

II comprising:

reacting magnetic particles M carrying amino groups with a maleimido-spacer, which reacts with amino groups, wherein X is selected from the group consisting of —(CH$_2$)$_3$—, phenylene, cyclohexane—CH$_2$—, and —CH$_2$—CH$_2$—CH$_2$—phenylene and said reaction forms an amide linkage between said maleimido-spacer and said amino groups to give a compound of the formula II and finally reacting said compound of the formula II with an immunoglobulin Ig having mercapto groups present in its hinge region, said mercapto groups produced by the reduction of interchain disulfide linkages, to give a compound of the formula I.

* * * * *